United States Patent [19]

Urdea

[11] Patent Number: 5,200,314
[45] Date of Patent: Apr. 6, 1993

[54] POLYNUCLEOTIDE CAPTURE ASSAY EMPLOYING IN VITRO AMPLIFICATION

[75] Inventor: Michael Urdea, Alamo, Calif.

[73] Assignee: Chiron Corporation, Emeryville, Calif.

[21] Appl. No.: 497,938

[22] Filed: Mar. 23, 1990

[51] Int. Cl.$^5$ .................. C12Q 1/68; C07H 15/12
[52] U.S. Cl. .................. 435/6; 435/210; 435/91; 536/24.3; 536/24.33; 935/77; 935/78; 436/94
[58] Field of Search .............. 435/6, 91, 810; 536/27, 536/5; 935/78, 77; 436/501, 94

[56] References Cited

U.S. PATENT DOCUMENTS

| | | | |
|---|---|---|---|
| 4,486,539 | 12/1984 | Ranki et al. | 436/504 |
| 4,563,419 | 1/1986 | Ranki et al. | 435/6 |
| 4,683,195 | 7/1987 | Mullis et al. | 435/6 |
| 4,683,202 | 7/1987 | Mullis et al. | |
| 4,725,536 | 2/1988 | Fritsch et al. | 435/6 |
| 4,766,062 | 8/1988 | Diamond et al. | 435/6 |
| 4,766,064 | 8/1988 | Williams et al. | 435/6 |
| 4,795,701 | 1/1989 | Vary | 435/6 |
| 4,818,680 | 4/1989 | Collins et al. | |
| 4,868,105 | 9/1989 | Urdea | |
| 5,124,246 | 6/1992 | Urdea et al. | 435/6 |

FOREIGN PATENT DOCUMENTS 0192168 11/1986 European Pat. Off. .
8403520 9/1984 PCT Int'l Appl. .

OTHER PUBLICATIONS

European Patent Application No. 124221 (Nov. 7, 1984).
European Patent Application No. 204510 (Dec. 10, 1986).

Primary Examiner—Robert A. Wax
Assistant Examiner—Miguel Escallon
Attorney, Agent, or Firm—Morrison & Foerster

[57] ABSTRACT

An analyte polynucleotide strand having an analyte sequence is detected within a sample containing polynucleotides by contacting the analyte polynucleotide with a capture probe under hybridization conditions, where the capture probe has a first binding partner specific for a solid-phase second binding partner. The resulting duplex is then immobilized by specific binding between the binding partners, and non-bound polynucleotides are separated from the bound species. The analyte polynucleotide is optionally displaced from the solid phase, then amplified by PCR. The PCR primers each have a polynucleotide region capable of hybridizing to a region of the analyte polynucleotide, and at least one of the primers further has an additional binding partner capable of binding a solid-phase binding partner. The amplified product is then separated from the reaction mixture by specific binding between the binding partners, and the amplified product is detected.

24 Claims, 3 Drawing Sheets

POLYNUCLEOTIDE CAPTURE ASSAY EMPLOYING IN VITRO AMPLIFICATION

TECHNICAL FIELD

This invention relates to the fields of nucleic acid chemistry and biochemical assays. More particularly, the invention relates to novel polynucleotide amplification and detection methods and reagents.

BACKGROUND OF THE INVENTION

Nucleic acid hybridizations are now commonly used in genetic research, biomedical research and clinical diagnostics. In the basic nucleic acid hybridization assay, single-stranded analyte nucleic acid (either DNA or RNA) is hybridized to a labeled nucleic acid probe, and resulting labeled duplexes are detected. Both radioactive and non-radioactive labels have been used.

Variations of this basic scheme have been developed to facilitate separation of the duplexes to be detected from extraneous materials and/or to amplify the signal that is detected.

Copending commonly owned U.S. Ser. No. 807,624, filed 11 Dec. 1985, described a solution-phase nucleic acid hybridization assay in which the analyte nucleic acid is hybridized to a labeling probe set and to a capturing probe set. The probe-analyte complex is coupled by hybridization with a solid-supported capture probe that is complementary to the capture probe set. This permits the analyte nucleic acid to be removed from solution as a solid phase complex. Having the analyte in the form of a solid phase complex facilitates subsequent separation steps in the assay. The labeling probe set is complementary to a labeled probe that is bound through hybridization to the solid phase/analyte complex.

PCT Application 84/03520 and EPA 124221 described a DNA hybridization assay in which analyte is annealed to a single-stranded DNA probe having a tail that is complementary to an enzyme-labeled oligonucleotide, and (2) the resulting tailed duplex is hybridized to an enzyme-labeled oligonucleotide. The Enzo Biochem "Bio-Bridge" labeling system appears to be similar to the system described in these two patent applications. The "Bio-Bridge" system uses terminal deoxynucleotide transferase to add unmodified 3'-polyT-tails to a DNA probe. The polyT-tailed probe is hybridized to the target DNA sequence and then to a biotin-modified polyA.

EPA 204510 describes a DNA hybridization assay in which analyte DNA is contacted with a probe that has a tail, such as a poly-dT tail, an amplifier strand that has a sequence, e.g., a poly-dA sequence, that hybridizes to the tail of the probe and is capable of binding a plurality of labeled strands.

Collins et al, U.S. Pat. No. 4,818,680, disclosed a polynucleotide displacement assay in which the target DNA sequence displaces a labeled signal strand from a partially double-stranded probe. The displaced signal strand is captured by hybridization to a capture probe, and the amount of labeled signal strand left after washing is quantified.

Vary, U.S. Pat. No. 4,795,701, disclosed another polynucleotide displacement assay, in which the signal strand is preferably RNA, thus making the probe reagent a DNA/RNA probe/signal strand heteroduplex. The amount of signal strand displaced is quantified by digesting the displaced strand to individual nucleotides, converting the ADP so produced to ATP, and assaying the ATP by its reaction with luciferase. The drawbacks to this method are that it depends upon complete digestion of only the displaced signal strands, it is subject to high background levels from ATP naturally present in the sample, and that the signal will vary with the adenosine content of the signal strand.

The main problem with these prior hybridization assays is that they lack sufficient specificity and/or signal to be useful for detecting very low levels of analyte. A primary object of the present invention is to provide amplification for use in nucleic acid hybridizations that provides a high reproducible gain in signal, a high reproducible signal-to-noise ratio and low nonspecific binding, that is itself reproducible, and that is capable of combining specifically with a "universal" signal moiety and an analyte at low concentrations to form a stable complex.

An improvement in DNA amplification, the polymerase chain reaction (PCR) technique, was disclosed by Mullis in U.S. Pat. Nos. 4,683,195 (Mullis et al) and 4,683,202, incorporated herein by reference. In the PCR technique, short oligonucleotide primers are prepared which match opposite ends of a desired sequence. The sequence between the primers need not be known. A sample of DNA (or RNA) is extracted and denatured (preferably by heat). Then, oligonucleotide primers are added in molar excess, along with dNTPs and a polymerase (preferably Taq polymerase, which is stable to heat). The DNA is replicated, then again denatured. This results in two "long products," which begin with the respective primers, and the two original strands (per duplex DNA molecule). The reaction mixture is then returned to polymerizing conditions (e.g., by lowering the temperature, inactivating a denaturing agent, or adding more polymerase), and a second cycle initiated. The second cycle provides the two original strands, the two long products from cycle 1, two new long products (replicated from the original strands), and two "short products" replicated from the long products. The short products have the sequence of the target sequence (sense or antisense) with a primer at each end. On each additional cycle, an additional two long products are produced, and a number of short products equal to the number of long and short products remaining at the end of the previous cycle. Thus, the number of short products grows exponentially with each cycle. This amplification of a specific analyte sequence allows the detection of extremely small quantities of DNA.

The recent advent of PCR technology has enabled the detection of specific DNA sequences present in extremely minute ($< 1$ fg) quantities. However, in order to obtain accurate results near the detection limit, great care must be exercised to avoid contamination with foreign DNA. It is possible to amplify DNA present on the glassware or in the reagents rather than the DNA originating in the sample, thus producing erroneous results.

DISCLOSURE OF THE INVENTION

The present invention overcomes the difficulties and disadvantages of the current assay methods. The present invention provides purification of the target sequence and rapid detection of the PCR product. In the method of the invention, a sample containing polynucleotides is assayed for an analyte polynucleotide strand by contacting the sample with a capture probe(s) capable of hybridizing to the analyte sequence under hybridization conditions to form an analyte-capture probe duplex, wherein the capture probe comprises an analyte-binding region and a first specific binding partner. The analyte-binding region is capable of hybridization with a region of the analyte polynucleotide, and the first specific binding partner is specific for a second binding partner. The second binding partner is immobilized on a first support. The duplex is then contacted with the immobilized second binding partner, thus immobilizing the duplex on the support. The non-bound polynucleotides are then removed from said sample, typically by washing. The analyte-capture probe complex may optionally be displaced from the support, and contacted with a first primer complementary to a first primer-binding region of the analyte polynucleotide under hybridizing conditions. Alternatively, the probe may be hybridized while bound to the support. A strand complementary to the analyte nucleotide is synthesized by nucleotide polymerization (for example using a nucleotide polymerase) to form an analyte-complementary strand duplex. The duplex is then denatured, and both strands contacted with primers (the complementary strand being contacted with a second primer capable of hybridizing to the complementary strand), followed by generation of a copy of the analyte sequence and another copy of the complementary strand. These duplexes are then denatured, and the process repeated until a detectable amount of polynucleotide is present. The polynucleotide is then detected, indicating the presence of the analyte sequence.

MODES OF CARRYING OUT THE INVENTION

A. Definitions

Figure 1A:
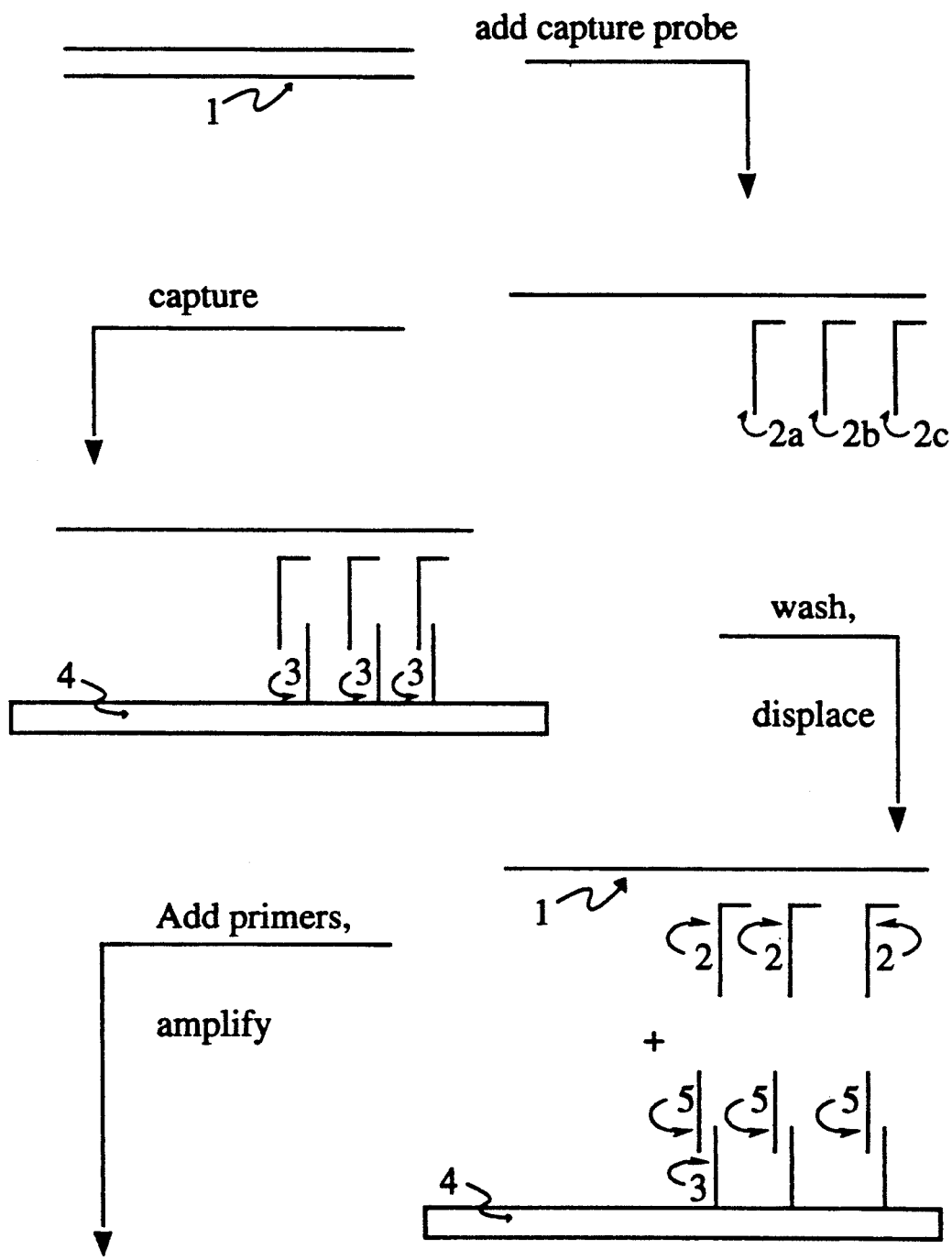
FIGS. 1a and 1b schematically depict the method of the invention.

The term "oligonucleotide" as used herein in referring to primers, probes, oligomer fragments to be detected, oligomer controls and unlabeled blocking oligomers is defined as a molecule comprised of two or more deoxyribonucleotides or ribonucleotides, preferably more than three. Its exact size will depend on many factors, which in turn depend on the ultimate function or use of the oligonucleotide.

The term "primer" as used herein refers to an oligonucleotide which is capable of acting as a point of initiation of synthesis when placed under appropriate conditions. The primer will be completely or substantially complementary to a region of the polynucleotide strand to be copied. Thus, under conditions conducive to hybridization, the primer will anneal to the complementary region of the analyte strand. Upon addition of suitable reactants (e.g., a DNA polymerase, nucleotide triphosphates, and the like), the primer is extended by the polymerase to form a copy of the analyte strand. The primer is preferably single stranded for maximum efficiency in amplification, but may alternatively be partially or fully double stranded. Preferably, the primer is an oligodeoxyribonucleotide. The primer must be sufficiently long to prime the synthesis of extension products in the presence of the polymerase. The exact lengths of the primers will depend on many factors, including temperature, solutes and the like. For example, for diagnostic applications, depending on the complexity of the analyte sequence, the oligonucleotide primer typically contains 15-25 or more nucleotides, although it may contain fewer nucleotides. Short primers generally require cooler temperatures to form sufficiently stable hybrid complexes with the template.

The primers herein are selected to be "substantially" complementary to the different strands of each target polynucleotide sequence to be amplified. This means that the primers must be sufficiently complementary to hybridize with their respective strands under the polymerization conditions. Therefore, the primer sequence need not reflect the exact sequence of the template. For example, a non-complementary nucleotide sequence may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer.

The primers used in presently preferred embodiments of the invention comprise a polynucleotide region capable of priming the DNA polymerase reaction, coupled to a specific binding partner as described below.

The terms "analyte polynucleotide" and "analyte strand" refer to a single- or double-stranded nucleic acid molecule which may be present in a biological sample. The term "analyte-complementary strand" refers to a polynucleotide strand which begins with the first primer and extends in the direction of polymerase action, and forms a strand complementary to that portion of the analyte polynucleotide. The term "analyte copy strand" refers to a polynucleotide complementary to the analyte-complementary strand (and thus substantially identical to the original analyte polynucleotide), having a second primer at its beginning and extending to the beginning of the region complementary to the first primer. The term "analyte copy/complementary duplex polynucleotide" refers to the double-stranded molecule consisting of the analyte copy strand hybridized to the analyte complementary strand.

The term "binding partner" as used herein refers to a molecule capable of binding a ligand molecule with high specificity, as for example in the case of an antigen and a monoclonal antibody specific therefor. In general, the specific binding partners must bind with sufficient affinity to immobilize the analyte copy/complementary strand duplex (in the case of capture probes) under the reaction and separation conditions. Other specific binding partners include biotin and avidin or streptavidin, IgG and protein A, and the numerous receptor-ligand couples known in the art. In the practice of the invention, the presently preferred binding partners are complementary polynucleotide strands. The specific binding polynucleotide region of the capture probe is preferably at least about 15-40 bases in length, and has a GC content of about 40-60%. The polynucleotides may be composed of DNA, RNA, or synthetic DNA analogs.

The term "capture probe" as used herein refers to a molecule comprising a single stranded polynucleotide coupled to a binding partner. The single-stranded polynucleotide region is complementary to a region of the analyte polynucleotide, and is sufficiently long and matched to afford sufficient affinity to immobilize the analyte polynucleotide to a solid surface (via the binding partners). The binding partner is specific for a second binding partner bound to the surface of a solid support.

The term "coupled" as used herein refers to attachment by covalent bonds or by strong non-covalent bonds (e.g., by strong ligand-receptor binding and related interactions). Covalent bonds may be ester, ether, phosphoester, amide, peptide, imide, carbon-sulfur bonds, carbon-phosphorous bonds, and the like, and are presently preferred. One may employ any labeling/linkage technology known in the art in the practice of the present invention.

The term "support" refers to any solid or semisolid surface to which a specific binding partner may be anchored. Suitable supports include glass, plastic, metal, polymer gels, and the like, and may take the form of beads, wells, dipsticks, membranes, and the like. Presently preferred supports are provided as polystyrene beads or microtiter dish wells.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, X-ray diffraction or absorption, magnetism, enzymatic activity, and the like. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a probe with biotin, and detect its presence with avidin labeled with $^{125}I$, or with an antibiotin MAb labeled with HRP. Other permutations and possibilities will be readily apparent to those of ordinary skill in the art, and are considered as equivalents within the scope of the instant invention.

The phrase "specific hybridization" refers to strict hybridization conditions in which exact complementarity between probe and sample analyte sequence is required. Such conditions are readily discernible by those of ordinary skill in the art, and depend upon the length and base composition of the sequence. In general, one may vary the temperature, ionic strength, and concentration of chaotropic agent(s) in the hybridization solution to obtain conditions under which substantially no sequences will hybridize in the absence of an "exact match." For hybridization of sequences to bound DNA, the empirical formula for calculating optimum temperature under standard conditions (0.9M NaCl) is $$T(°C) = 4(N_G + N_C) + 2(N_A + N_T) - 5° C.,$$

where $N_G$, $N_C$, $N_A$, and $N_T$ are the numbers of G, C, A, and T bases in the sequence (J. Meinkoth et al, *Anal Biochem* (1984) 138:267-84).

B. General Method

The capture probe and primers are prepared by conventional nucleic acid synthesis techniques.

The method of the invention may be practiced as follows. A sample containing analyte nucleic acid (preferably single-stranded) is incubated under hybridization conditions with an excess of single-stranded nucleic acid capture probes (or probe sets), having a first binding sequence complementary to the analyte and a displaceable first binding partner specific for a solid-phase second binding partner, preferably a binding polynucleotide that is complementary to a single-stranded oligonucleotide bound to the solid phase. The result is an analyte polynucleotide having one or more probes bound thereto. The second binding sequences of the probes remain as single-stranded tails as they are not complementary to the analyte. Multiple probes of each type may be used, and may have identical or different hybridizing sequences, and identical or different binding partners. It is presently preferred to employ a plurality of non-overlapping capture probes (a capture probe set).

This complex is then added under binding conditions to a solid phase having a second specific binding partner, preferably a single-stranded oligonucleotide bound to it that is complementary to the binding sequence of the capture probe. Where a capture probe set is employed, it is preferred to use identical binding partners, particularly where the first and second binding partners are polynucleotides (i.e., each of the capture probes would have a unique analyte-binding region, but would share the same first binding partner sequence). The resulting product comprises the complex bound to the solid phase via the duplex formed by the oligonucleotide bound to the solid phase and the second binding sequence of the capture probe. The solid phase with bound complex is then separated from unbound materials, generally by washing.

After separation of unbound materials, the analyte polynucleotide may optionally be displaced from the solid support. Where the first and second binding partners are oligonucleotides, this displacement may be effected by adding an oligonucleotide having a higher affinity for either the first binding partner or the second binding partner, and allowing the displacing oligonucleotide to hybridize with the binding partner (see for example, Vary, U.S. Pat. No. 4,795,701, supra, regarding probe displacement). The affinity of the various oligonucleotides may be adjusted by increasing probe length and fidelity of base-pair matching to increase affinity, or reducing length and permitting mismatches to reduce affinity. Where the first and second binding partners are proteins, displacement may generally be effected by competition with a ligand of higher affinity (or higher concentration), by altering buffer conditions (for example, by increasing or decreasing solute concentrations, changing solvent, and the like), or by application of an appropriate protease. Alternatively, one may continue without displacement under appropriate conditions. It is generally possible to conduct PCR amplification of the target sequence where the target sequence is spaced a sufficient distance from the region of the analyte bound to the solid support, i.e., where there is sufficient separation between the primer binding regions and the capture probe binding regions. If it is desired to amplify the target sequence without prior displacement, the primer binding regions and capture probe binding regions should be selected at least 500 bp apart.

The analyte nucleic acids may be obtained from a variety of sources, including biological fluids and solids, food stuffs, environmental materials, forensic and archaeological specimens, etc., and may be prepared for the hybridization analysis by a variety of means, e.g., proteinase K/SDS, chaotropic salts, and the like. Also, it may be of advantage to decrease the average size of the analyte nucleic acids by enzymatic, physical or chemical means, for example, by restriction enzymes, sonication, chemical degradation (e.g., metal ions), and the like. The fragments may be as small as 0.1 kb, but are usually at least about 0.5 kb and may be 1 kb or higher. The analyte sequence is preferably provided in single-stranded form for analysis. Where the sequence is naturally present in single-stranded form, denaturation is usually not required unless significant secondary structure is present. However, where the sequence is present in double-stranded form, the sequence should first be denatured. Denaturation can be carried out by various techniques, such as alkali treatment, generally from about 0.05 to 0.2M hydroxide, formamide, salts, heat, or combinations thereof.

The sequence of the capture probe complementary to the analyte sequence will each be of at least 15 nucleotides (nt), usually at least 25 nt, and preferably not more than about 5 kb, usually not more than about 1 kb, preferably not more than about 100 nt. They will typically be approximately 30–50 nt. They will normally be chosen to bind to different sequences of the analyte. The analyte-binding sequences may be selected based on a variety of considerations. Depending upon the nature of the analyte, one may be interested in a consensus sequence, a sequence associated with polymorphisms, a particular phenotype or genotype, a particular strain, or the like.

By appropriate selection of the analyte-binding sequences of the capture probe or probe set a specific nucleic acid molecule that includes a particular gene or other sequence that is present as part of different nucleic acid molecules may be identified. In order to discriminate the nucleic acid molecule of interest from other molecules that also contain the given sequence, one of the probes is made complementary to the given sequence while the other is made complementary to another sequence of the molecule which other sequence is unique to that molecule (i.e., is not present in the other molecules that contain the given sequence).

The specific binding partner of the capture probe is selected to bind specifically to the second binding partner attached to the solid phase and so as to not be encountered by endogenous components in the sample/analyte. It is presently preferred to employ oligonucleotide sequences as first and second binding partners. The binding sequence may be contiguous to the analyte-binding sequence in the capture probe or may be spaced therefrom by an intermediate noncomplementary sequence. The probes may include other noncomplementary sequences if desired. These noncomplementary sequences must not hinder the binding of the binding sequences or cause nonspecific binding to occur. The capture probe may be prepared by oligonucleotide synthetic procedures or by cloning, preferably the former.

It will be appreciated that the binding sequences need not have perfect complementarity to provide homoduplexes. In many situations, heteroduplexes will suffice where fewer than about 10–30% of the bases are mismatches, ignoring loops of five or more nucleotides. Accordingly, as used herein the term "complementary" intends a degree of complementarity sufficient to provide a stable duplex structure. In some embodiments of the invention it is preferred to use heteroduplexes, so that one may displace the binding partner by hybridization with a polynucleotide having greater complementarity.

The solid phase that is used in the assay may be particulate or solid, particularly the solid wall surface of any of a variety of containers, e.g., centrifugal tubes, columns, microtiter plate wells, filters, tubing, etc. When particles are used, they will preferably be of a size in the range of about 0.4 to 200 microns, more usually from about 0.8 to 4.0 $\mu$m. The particles may be any convenient material, such as latex, polystyrene or glass. Polystyrene beads and microtiter plates are the presently preferred solid surfaces. The solid phase binding partner may be stably attached to the support surface through functional groups by known procedures.

The labeled oligonucleotide can be conveniently prepared by chemical synthesis. By providing a terminal group which has a convenient functionality, various labels may be joined through the functionality. Thus, one can provide a carboxy, thiol, amine, hydrazine or other functionality to which the various labels may be joined without detrimentally affecting duplex formation with the sequence. The use of amines is presently preferred (see M. Urdea et al, *Nuc Acids Res* (1988) 16:4937–56). As already indicated, one can have a molecule with a plurality of labels joined to the sequence complementary to the labeling sequence. Alternatively, one may have a ligand bound to the labeling sequence and use a labeled receptor for binding to the ligand to provide the labeled analyte complex.

The ratio of capture probe and labeled probe to anticipated moles of analyte will each be at least stoichiometric and preferably in excess. It will normally be in the range of 2:1 to 10,000:1. Concentrations of each of the probes will generally range from about $10^{-9}$ to $10^{-6}$ M, with sample nucleic acid concentrations varying from $10^{-21}$ to $10^{-12}$ M. The hybridization steps of the assay will generally take from about 10 minutes to 2 hours, frequently being completed in about 15 min. Hybridization can be carried out at a mildly elevated temperature, generally in the range from about 20° C. to 80° C., more usually from about 35° C. to 70° C., particularly 65° C.

The hybridization reaction is usually done in an aqueous medium, particularly a buffered aqueous medium, which may include various additives. Additives which may be employed include low concentrations of detergent (0.1 to 1%), salts, e.g., sodium citrate (0.017 to 0.170M), Ficoll, polyvinylpyrrolidine, carrier nucleic acids, carrier proteins, etc. Nonaqueous solvents may be added to the aqueous medium, such as dimethylformamide, dimethylsulfoxide, alcohols, and formamide. These other solvents may be present in amounts ranging from about 2 to 50%.

The stringency of the hybridization medium may be controlled by temperature, salt concentration, solvent system, and the like. Thus, depending upon the length and nature of the sequence of interest, the stringency will be varied.

The procedure used in the separation steps of the assay will vary depending upon the nature of the solid phase. For particles, centrifugation or filtration provides a convenient separation of the particles, discarding the supernatant or isolating the supernatant. Where the particles are assayed, the particles will be washed thoroughly, usually from one to five times, with an appropriate buffered medium, e.g., PBS containing a detergent such as SDS or NP40. When the separation means is a wall or support, the supernatant may be isolated or discarded and the wall washed in the same manner as indicated for the particles.

Suitable primers are prepared by means known to those of ordinary skill in the art, for example by cloning and restriction of appropriate sequences, or by direct chemical synthesis. For example, one may employ the phosphotriester method described by S. A. Narang et al, *Meth Enzymol* (1979) 68:90, and U.S. Pat. No. 4,356,270, incorporated herein by reference. Alternatively, one may use the phosphodiester method disclosed in E. L. Brown et al, *Meth Enzymol* (1979) 68:109, incorporated herein by reference. Other methods include the phosphoramidite method disclosed in Beaucage et al, *Tetrahedron Lett* (1981) 22:1859-62, and the solid support method in U.S. Pat. No. 4,458,066. The primers may also be labeled, if desired, by incorporating means detectable by spectroscopic, photochemical, biochemical, immunochemical, or chemical means. For example, the primer may include $^{32}P$, fluorescent dyes, electron-dense reagents, enzymes (as commonly used in ELISAs), biotin, or haptens or proteins for which antisera or monoclonal antibodies are available. The label should be selected to withstand denaturing conditions if it is to be attached directly to the primer.

When the analyte strand has been separated from contaminating material, and has been displaced from the solid support (if desired), it is ready to be used as a template for the synthesis of additional nucleic acid strands. This synthesis can be performed using any suitable method. The reaction is generally conducted in a buffered aqueous solution, preferably at a pH of 7-9, most preferably about 8. Preferably, a molar excess (for cloned nucleic acid, usually about 1000:1 primer/template, and for genomic or viral nucleic acid, usually about 108:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

It is important that the primers used include a means for halting transcription between the analyte-hybridizing region and the capture or probe-binding region. It is presently preferred to join the analyte-hybridizing region and the capture or probe-binding region by means of the arresting linker described herein. However, other methods are applicable. For example, any linker joining the probe segments, or derivatization of the bases near the junction, which prevents the selected polymerase from continuing replication may be used.

The deoxyribonucleoside triphosphates dATP, dCTP, dGTP and dTTP are also added to the synthesis mixture in adequate amounts and the resulting solution is heated to about 90°-100° C. for about 1 to 10 minutes, preferably from 1 to 4 minutes. After heating, the solution is allowed to cool to room temperature, which is preferred for the primer hybridization. To the cooled mixture is added a polymerization agent, and the reaction is conducted under conditions known in the art. This synthesis reaction may occur at from room temperature up to a temperature above which the polymerization agent no longer functions efficiently. Thus, for example, if an *E. coli* DNA polymerase is used as the polymerizing agent, the maximum temperature is generally no greater than about 40° C. Most conveniently, the reaction using *E. coli* polymerase occurs at room temperature. Where greater stringency is desired, the reaction is performed using the thermostable enzyme Taq polymerase at elevated temperature.

The polymerization agent may be any compound or system which will function to accomplish the synthesis of primer extension products from nucleotide triphosphates, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes such as Taq polymerase, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be agents, however, which initiate synthesis at the 5' end and proceed in the other direction, using the same process as described above: use of such agents in the process of the invention is also to be considered within the scope of this invention.

The newly synthesized analyte-complementary strand and the original analyte nucleic acid strand form a double-stranded molecule which is used in the succeeding steps of the process. In the next step, the strands of the duplex molecule are separated using any of the procedures described above to provide single-stranded molecules.

New nucleic acid is synthesized on the single-stranded molecules. Additional polymerization agent, nucleotides and primers may be added if necessary for the reaction to proceed under the conditions prescribed above. Again, the synthesis will be initiated at one end of the oligonucleotide primers and will proceed along the single strands of the template to produce additional nucleic acid. After this step, half of the extension product will consist of the specific nucleic acid sequence bounded by the two primers.

The steps of strand separation and extension product synthesis can be repeated as often as needed to produce the desired quantity of the specific nucleic acid sequence. As will be described in further detail below, the amount of the specific nucleic acid sequence produced will accumulate in an exponential fashion.

Figure 2:
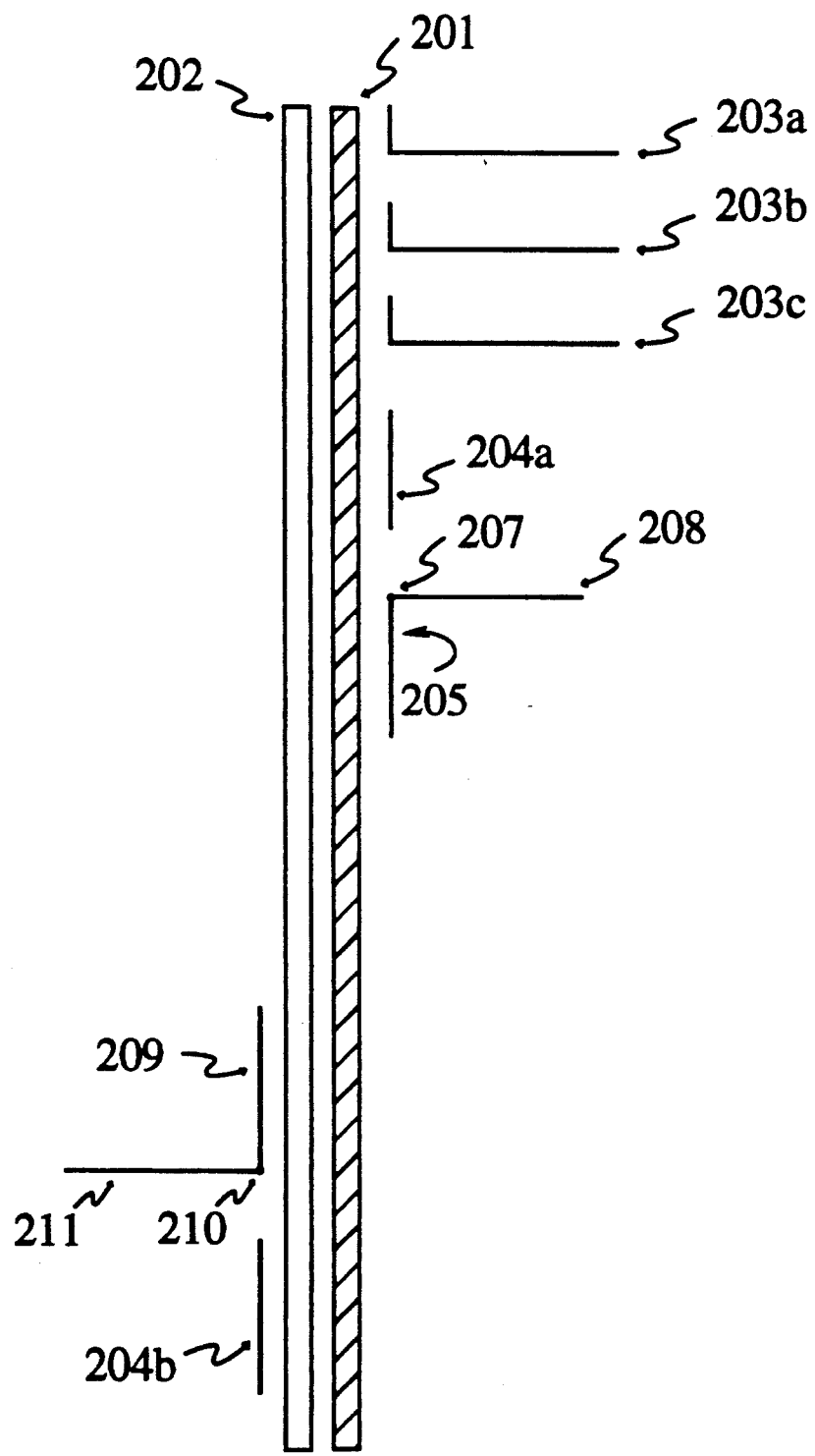
FIG. 2 schematically depicts the hybridization of the capture probes and primers of the invention to an analyte polynucleotide and its complement.

If desired, one may amplify the target sequence in two stages, using nested primers. This variation may be used as a means for increasing the specificity of the reaction. The first phase of PCR may be performed with "normal" primers, i.e., primers which do not arrest polymerization, while the second phase is performed with the arresting primers of the invention. The primer binding regions are selected so that the second set (arresting primers) bind to regions of the analyte sequence between the primer binding regions for the first set (thus insuring that the second set binding regions will be amplified if present). FIG. 2 illustrates such an arrangement. The analyte polynucleotide and its complement are indicated by 201 and 202. Hybridizing to one end of the analyte polynucleotide are capture probes 203a, 203b, and 203c, having unique hybridizing regions and sharing a common sequence for the "tails." Primers 204a and 204b are conventional primers, used for the first (optional) round of PCR amplification. Primers 205 and 209 hybridize to the region of the analyte and complement which is bounded by the conventional primer binding regions. Primers 205 and 209 each have arresting linkers 207 and 210, which prevent polymerization of the specific binding partner regions 208 and 211 of the primers.

The amplification process may be terminated at any time once a detectable quantity of polynucleotide has accumulated. In general, suitable detection means are employed to determine the presence and/or quantity of target sequence present in the amplified reaction mixture. Presence of the target sequence in the sample is generally determined by the presence or absence of binding by a labeled probe. In one embodiment of the invention, a labeled oligonucleotide is provided which is complementary to a sequence present in the analyte copy strand and/or analyte complementary strand. In this embodiment, the analyte copy/complementary duplex is denatured, the probe added, the probe-strand complex separated from non-bound probe, and the label detected. Alternatively, the first or second primer may carry a third binding partner attached thereto, which is capable of binding to a fourth binding partner attached to a label. In a presently preferred embodiment, the third and fourth binding partners are complementary oligonucleotides: the labeled probe hybridizes to an extension of the first or second primer which does not hybridize to the analyte copy or complementary sequence. Separation may be effected by conventional means, for example gel chromatography or the like. However, it is presently preferred to separate product duplexes by binding a fifth specific binding partner attached to the first or second primer to a sixth specific binding partner attached to a support. The presently preferred fifth and sixth binding partners are again complementary oligonucleotide sequences.

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels which have been employed in immunoassays and the techniques applicable to immunoassays can be employed with the subject assays.

Kits for carrying out amplified nucleic acid hybridization assays according to the invention will comprise in packaged combination at least the following reagents: a capture probe, a first support capable of binding the capture probe, and first and second primers specific for the analyte polynucleotide. The kit will preferably also include a labeled probe capable of binding to the first or second primer, and displacement means (e.g., a displacing oligonucleotide) for releasing the bound analyte from the solid surface prior to amplification. These reagents will typically be provided in separate containers in the kit. The kit may also include a DNA polymerase such as *E. coli* DNA Polymerase I (Klenow fragment), Taq polymerase or the like, a denaturation reagent for denaturing the analyte, hybridization buffers, wash solutions, enzyme substrates, negative and positive controls and written instructions for carrying out the assay.

C. EXAMPLES

The examples presented below are provided as a further guide to the practitioner of ordinary skill in the art, and are not to be construed as limiting the invention in any way.

EXAMPLE 1

Preparation of Arresting Linkers

The linkers described herein are used to join the analyte-hybridizing region and the capture or probe-binding region of the probes and primers of the invention in such a manner that the nucleotide polymerase used cannot read through the linkage. Replication is halted at the arresting linker.

The following abbreviations are used in this section: DMT=dimethoxytrityl; T=deoxythymidine; DMF=dimethylformamide; BDMS=t-butyldimethylsilyl; C=deoxycytidine; TLC=thin-layer chromatography; DMAP=N,N-dimethylaminopyridine; THF=tetrahydrofuran; DIPEA=diisopropylethylamine; LEV=levulinic ester; DCA=dichloroacetic acid; DCC=dicyclohexylcarbodiimide; DCHU=dicyclohexylurea; TEA=triethylamine; TMS=trimethylsilyl; FMOC=9-fluorenylmethoxycarbonyl.

A. Synthesis of Arresting Linker:

5-DMT-T-OH (27.3 g, 50 mmole) and imidazole (10 g, 150 mmole) were coevaporated with 200 mL DMF. The residue was dissolved in 250 mL DMF, and BDMS chloride (75 mmol) was added. The reaction mixture was stirred for 18 hr at 20° C. Methanol (50 mL) was added and after 30 min the solvents were removed in vacuo. The oily residue was dissolved in 50 mL ethyl acetate, and the organic phase extracted with 5% aqueous $NaHCO_3$ (2×500 mL) and 80% saturated aqueous NaCl (500 mL) and finally dried over solid $Na_2SO_4$. The solvent was removed in vacuo to give 35 g (50 mmole) 5'-DMT-3'BDMS T (100% yield). This material was used without further purification.

Triazole (25.6 g) was suspended in 400 mL of $CH_3CN$ at 0° C. and $POCl_3$ (8 mL) was added with rapid stirring. Then triethylamine (60 mL) was added dropwise over 15 min to the slurry stirred at 0° C. for 30 min. 5'-DMT-3'BDMS T (25 mmole crude) dissolved in 100 mL $CH_3CN$ was added dropwise to the stirred slurry at 0° C. The ice-water bath was removed and stirring continued at 20° C. for one hour. The reaction mixture was diluted with 800 mL ethyl acetate, and the organic phase was extracted with 5% $NaHCO_3$ (2×500 mL) and 80% saturated aqueous NaCl (500 mL). After drying the organic phase over solid $Na_2SO_4$, solvents were removed in vacuo. The resulting residue was coevaporated with toluene (400 mL) and $CH_3CN$ (400 mL) to give 5'-DMT-3'-BDMS-5-methyl-4-triazoyl β-D-2-deoxyribofuranosyl-2(1H)-pyrimidinone as a white foam in quantitative yield. This material was used without further purification.

To a solution of 6-aminohexanol (11.7 g, 100 mmole) in 400 mL $CH_3CN$ was added dropwise 5'-DMT-3'-BDMS-5-methyl-4-triazoyl β-D-2-deoxyribofuranosyl- 2(1H)-pyrimidinone (8.7 g, 12 mmole) dissolved in 100 mL CH$_3$CN and the reaction mixture stirred at 20° C. The progress of the reaction was monitored by TLC (every 30 min), and when the starting material had completely disappeared (usually in 1-2 hours), the reaction mixture was diluted with 500 mL ethyl acetate, which was extracted with 5% aqueous NaHCO$_3$ and 80% saturated aqueous NaCl as described above. After drying the organic phase over Na$_2$SO$_4$, the solvent was removed in vacuo to give 7.0 g (9.2 mmole) of product 5'-DMT-3'-BDMS-5-methyl-N$^4$-6-hydroxyhexyl deoxycytidine (yield 77%). This material was used without further purification.

To a solution of 5'-DMT-3'-BDMS-5-methyl-N$^4$-6-hydroxyhexyl deoxycytidine (7 g, 9.2 mmole) in 100 mL THF was added (CH$_3$COCH$_2$CH$_2$CO)$_2$O (50 mmole) dissolved in 100 mL THF and then 10 mL 6.5% DMAP in 2,6-lutidine/THF. The reaction mixture was left stirring for 30 min. TLC analysis showed that starting material had been completely consumed. The reaction mixture was diluted with 700 mL ethyl acetate which was diluted with 700 mL ethyl acetate, and extracted with 5% aqueous NaHCO$_3$ (3×500 mL) and 80% saturated aqueous NaCl (500 mL) as described above. After drying over solid Na$_2$SO$_4$, the solvent was removed and the residue coevaporated with toluene (200 mL) and CH$_3$CN (200 mL) to yield 12.3 g of crude product.

This crude product was dissolved in 100 mL THF, and 10 mL of a 1.1M solution of tetrabutylammonium fluoride in THF was added. The progress of the reaction was monitored by TLC; it is usually over in 30 min but may take longer. When starting material had been consumed, the reaction mixture was diluted with 700 mL ethyl acetate, and extracted with NaHCO$_3$ and NaCl solutions, as above. Removal of the solvent afforded 8.5 g crude product 5'-DMT-5-methyl-N$^4$(O-levulinyl-6-oxyhexyl)-2'-deoxycytidine. This material was subjected to silica gel chromatography. The purified product was isolated by elution with 4% methanol in CH$_2$Cl$_2$ to give 5.0 g of a slightly brownish foam (6.7 mmole; 73% yield).

Silica-purified 5'-DMT-5-methyl-N$^4$(O-levulinyl-6-oxyhexyl)-2'-deoxycytidine (7.7 mmole) was coevaporated twice with CH$_3$CN. The resulting dry powder was dissolved in 70 mL CH$_2$Cl$_2$ containing 4.9 mL DIPEA in a flask under argon. After cooling to 0° C., 1.65 mL (8.5 mmole) N,N-diisopropylaminomethoxy chlorophosphine was added with a syringe and the mixture stirred at 0° C. for 30 min. After dilution with 400 mL ethyl acetate, the organic phase was washed 4 times with 400 mL 80% saturated aqueous NaCl, then dried over solid Na$_2$SO$_4$ and filtered. The solvent was removed in vacuo and the resulting residue coevaporated twice with toluene to give an oil. This oil was dissolved in 30 mL toluene and added dropwise into 400 mL cold hexane (about −20° C.). The precipitate was quickly collected by filtration and dried in vacuo for 18 hr to give 5.45 g of phosphoramidite (6.0 mmole; 78% yield).

B. Synthesis of Alternative Arresting Linker

To a solution of 5'-DMT-3-BDMS-5-methyl-N$^4$-6-hydroxyhexyl deoxycytidine (34 g, 50 mmole) prepared as described above in 200 mL CH$_2$Cl$_2$ was added 1.5 g N,N-dimethylaminopyridine and 25 mL triethylamine. To this solution at 0° C. was added dropwise DMT-Cl (75 mmole, 25.5 g) dissolved in CH$_2$Cl$_2$ (100 mL). The reaction mixture was left stirring for 1 hour. The analysis showed that starting material had been completely consumed. Then 50 mL of MeOH was added. After 30 min the reaction mixture was diluted with 800 mL ethyl acetate which was extracted with 5% NaHCO$_3$ (2×500 mL) and 80% saturated aqueous NaCl (500 mL) as described above. After drying over solid Na$_2$SO$_4$, the solvent was removed in vacuo and the residue coevaporated with toluene (200 mL) and CH$_3$CH (200 mL).

This crude product was dissolved in 200 mL THF, and 200 mL of a 1.1M solution of tetrabutylammonium fluoride in THF was added. The progress of the reaction was monitored by TLC; it is usually over in 30 min but may take longer. When starting material had been consumed, the reaction mixture was diluted with 700 mL ethyl acetate, which was extracted with NaHCO$_3$ and NaCl solutions, as above. Removal of the solvent afforded 36 g crude product, 5'-DMT-5-methyl-N$^4$(O-DMT-6-oxyhexyl)deoxycytidine. This material was subjected to silica gel chromatography, and the purified product isolated by elution with 2-4% methanol in CH$_2$Cl$_2$ to provide 32.7 g of pure product (34 mmole; yield based on 5'-DMT-T-OH: 69%).

Silica-purified 5'-DMT-5-methyl-N$^4$(O-DMT-6-oxyhexyl)-2'-deoxycytidine (34 mmole) was coevaporated twice with CH$_3$CN. The resulting dry powder was dissolved in 100 mL CH$_2$Cl$_2$ containing 7.5 mL DIPEA in a flask under argon. After cooling to 0° C., 7.37 mL (38 mmole) N,N-diisopropylaminomethoxy chlorophosphine was added with a syringe and the mixture stirred at 0° C. for 30 min. After dilution with 800 mL ethyl acetate, the organic phase was washed 4 times with 800 mL 80% saturated aqueous NaCl, then dried over solid Na$_2$SO$_4$ and filtered. The solvent was removed in vacuo and the resulting residue coevaporated twice with toluene to give an oil. This oil was dissolved in 80 mL toluene and added dropwise into 700 mL cold hexane (about −20° C.). The precipitate was quickly collected by filtration and dried in vacuo for 18 hr to give 31.8 g of phosphoramidite (28.7 mmole; 84% yield).

5'-DMT-T-OH (16.4, 30 mmole) was dissolved in dry 200 mL CH$_3$CN and 1-(TMS)imidazole (14.6 mL, 100 mmole) was added. After 60 min the solvents were removed in vacuo. The oily residue was dissolved in 700 mL ethyl acetate, and the organic phase extracted with 5% aqueous NaHCO$_3$ (2×500 mL) and 80% saturated aqueous NaCl (500 mL) and finally dried over solid Na$_2$SO$_4$. The solvent was removed in vacuo to give 30 mmole 5'-DMT-3'-TMS-T (100% yield). This material was used without further purification.

Triazole (37.8 g) was suspended in 450 mL of CH$_3$CN (at 0° C.) and POCl$_3$ (12 mL) was added with rapid stirring. Triethylamine (90 mL) was added dropwise over 15 min to the slurry stirred at 0° C. for 30 min. 5'-DMT-3'-TMS-T (30 mmole crude) dissolved in 100 mL CH$_3$CN was added dropwise to the stirred slurry at 0° C. The ice-water bath was removed and stirring continued at 20° C. for one hour. The reaction mixture was diluted with 800 mL ethyl acetate, and the organic phase was extracted with 5% NaHCO$_3$ (2×500 mL) and 80% saturated aqueous NaCl (500 mL). After drying the organic phase over solid Na$_2$SO$_4$, solvents were removed in vacuo. The resulting residue was coevaporated with toluene (400 mL) and CH$_3$CN (400 mL) to give 5'-DMT-3'-TMS-5-methyl-4-triazoyl β-D-2-deoxyribofuranosyl-2(1H)-pyrimidinone as a white foam in quantitative yield. This material was used without further purification.

To a solution of 6-aminohexanol (23 g, 200 mmole) in 400 mL CH$_3$CN was added dropwise 5'-DMT-3'-TMS-5-methyl-4-triazoyl β-D-2-deoxyribofuranosyl-2(1H)-pyrimidinone (20 g, 30 mmole) dissolved in 100 mL CH$_3$CN and the reaction mixture stirred at 20° C. The progress of the reaction was monitored by TLC (every 30 min) and when the starting material had completely disappeared (usually in 1-2 hours), the reaction mixture was diluted with 800 mL ethyl acetate, which was extracted with 5% aqueous NaHCO$_3$ and 80% saturated aqueous NaCl as described above. After drying of the organic phase over Na$_2$SO$_4$, the solvent was removed in vacuo to give 20.3 g (~30 mmole) of product 5'-DMT-3'-TMS-5-methyl-N$^4$-6-hydroxyhexyl deoxycytidine. This material was used without further purification.

To a solution of 5'-DMT-3'-TMS-5-methyl-N$^4$(6-hydroxyhexyl)deoxycytidine in 250 mL methanol was added 25 mL concentrated aqueous NH$_4$OH and the reaction mixture left stirring in a closed round-bottom flask to 1 hour. The solvent was then removed in vacuo and coevaporated with 1×200 mL ethanol, 1×100 mL toluene and 1×100 mL CH$_3$CN to give 5'-DMT-5-methyl-N$^4$(6-hydroxyhexyl)deoxycytidine in quantitative yield. This material was used without further purification. This material was dissolved in 200 mL CH$_2$Cl$_2$, and 4 mL of pyridine was added followed by dropwise addition of FMOC-Cl (7.8 g, 30 mmole) dissolved in CH$_2$Cl$_2$ (50 mL). The reaction mixture was left stirring for 30 min. The analysis showed that starting material had been completely consumed. The reaction mixture was diluted with 500 mL ethyl acetate which was extracted with 5% aqueous NaHCO$_3$ (3×500 mL) and 80% saturated aqueous NaCl (500 mL) as described above. After drying over solid Na$_2$SO$_4$, the solvent was removed and the residue coevaporated with toluene (200 mL) and CH$_3$CN (200 mL) to give 23.7 g of crude product. This crude product was subjected to silica gel chromatography. The purified product eluted with about 4% methanol in CH$_2$Cl to give 13.3 g (15.3 mmole) of pure 5'-DMT-5-methyl-N$^4$(O-FMOC-6-oxyhexyl)deoxycytidine (50% yield based on 5'-DMT-TOH).

Silica-purified 5'-DMT-5-methyl-N$^4$(O-FMOC-6-oxyhexyl)-2'-deoxyoytidine (15.3 mmole) was coevaporated twice with CH$_3$CN. The resulting dry powder was dissolved in 60 mL CH$_2$Cl$_2$ containing 4.1 mL DIPEA in a flask under argon. After cooling to 0° C., 3.19 mL (16.5 mmole) N,N-diisopropylaminomethoxy chlorophosphine was added with a syringe and the mixture stirred at 0° C. for 30 min. After dilution with 400 mL ethyl acetate, the organic phase was washed 4 times with 400 mL 80% saturated aqueous NaCl, then dried over solid Na$_2$SO$_4$ and filtered. The solvent was removed in vacuo and the resulting residue coevaporated twice with toluene to give an oil. This oil was dissolved in 50 mL toluene and added dropwise into 400 mL cold hexane (about −20° C.). The precipitate was quickly collected by filtration and dried in vacuo for 18 hr to give 12.15 g of phosphoramidite (11.8 mmole; 77% yield). Removal of O-FMOC group during solid phase synthesis: t-butylamine/pyridine (1:10 v/v) for 1 hour at 20° C. Removal of 0-levulinyl group: 0.5M hydrazine hydrate in pyridine/glacial acetic acid (4:1 v/v) 15 minutes at 20° C.

EXAMPLE 2

Assay for Hepatitis B Virus

A. Standard Analyte HBV DNA

Figure 1B:
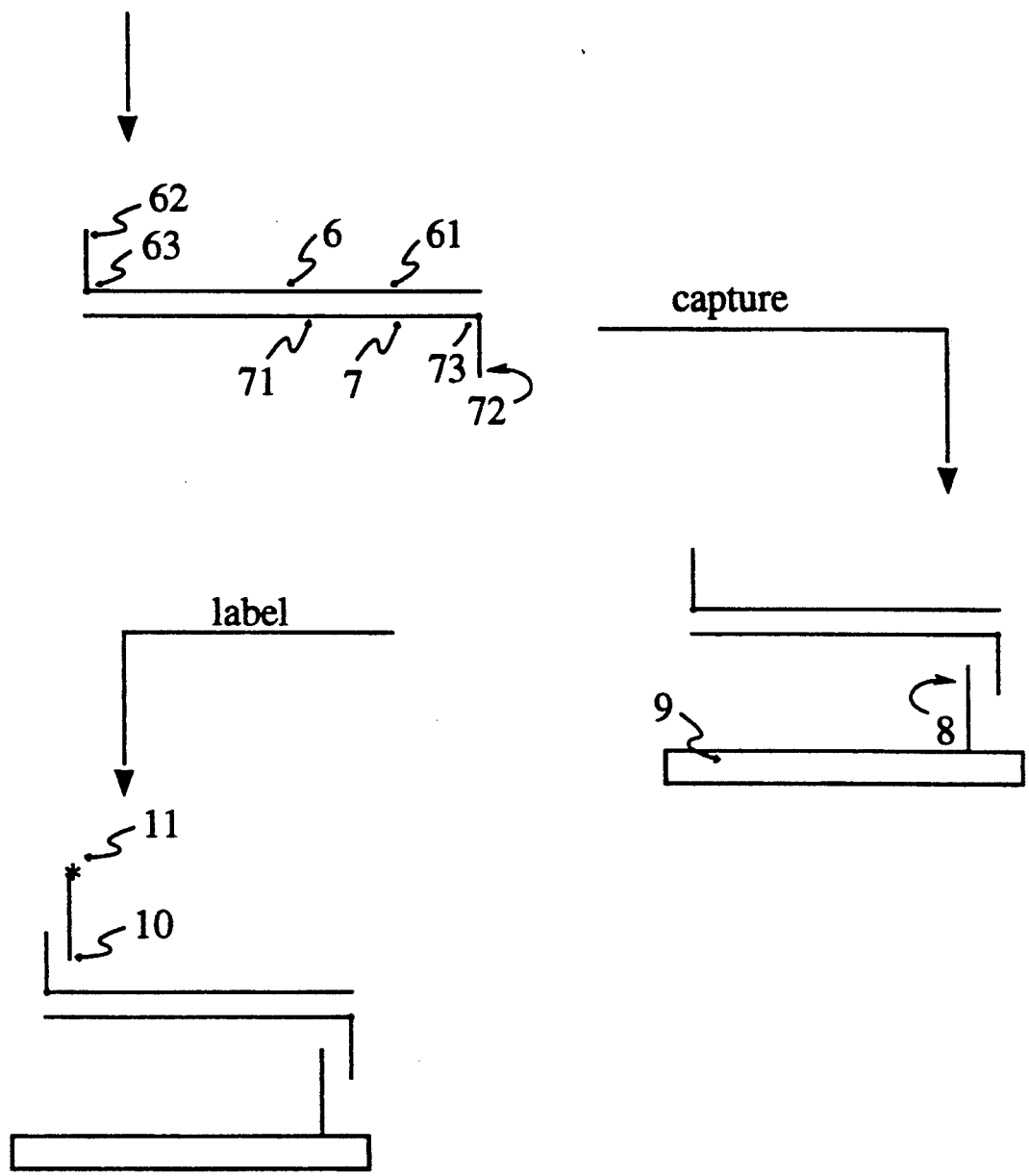

The plasmid pHE63 composed of the entire 3.2 kb HBV genome cloned into the EcoRI site of plasmid pBR325 linearized with EcoRI and diluted into normal human serum was used as standard analyte. The analyte is designated 1 in FIG. 1.

B. Solid Phase Probe

A 21 base oligomer, 5'-XCACCACTTTCT-CCAAAGAAG-3', where X represents the N$^4$-(2-aminoethyl) derivative of cytidine, was synthesized and biotinylated using N-hydroxysuccinimdyl biotin in 0.1M sodium phosphate, pH 7.5, as described in Urdea et al, U.S. Pat. No. 4,868,105, incorporated herein by reference. A 5 μL aliquot of this biotinylated fragment (800 pmoles) was added to a 1.5 mL Eppendorf tube containing 500 μL of 0.25% (w/v) 2.8 μm avidin polystyrene beads in 1× PBS. After a 1 h incubation at 37° C., the beads were washed 3 times with 500 μL of 0.1% SDS, 4× SSC by centrifugation then resuspended and stored in the same solution until used. The solid phase probe(s) is depicted as 3 and 8 in FIG. 1, bound to support surface (beads) 4 (9).

C. Labeling Probe

An 18 base oligomer, 5'-XGGTCCTAGCCT-GACAGC-3', where X is as defined above, was synthesized. Calf intestinal alkaline phosphatase (AP) 11 (3 mg in buffer; immunoassay grade, Boehringer-Mannheim) was placed in a Centricon 30 Microconcentrator. Approximately 2 mL of 0.1M sodium borate, pH 9.5, was then added and the device spun at 3500 rpm until a final volume of 40 μL was obtained. The alkylamino oligonucleotide was then activated with DITC, extracted with butanol, and combined with the protein. PAGE, elution (with 0.1M Tris, pH 7.5, 0.1M NaCl, 10 mM MgCl$_2$, 0.1 mM ZnCl$_2$), and concentration provided the final product, (10 in FIG. 1) which was stored at 4° C.

D. Capture Probes

A set of 5 single-stranded polynucleotides each having a varying 30-base long portion complementary to a specific sequence of the HBV genome and a constant 20 base long 3'-portion complementary to the oligonucleotide bound to the solid phase (part B above) was synthesized by the procedures described in part B above.

E. Primers

Primers 6 and 7 were also synthesized following the procedure of part B above. Primer 7 consists of a sequence 71 complementary to a portion of the HBV genome, a portion 72 complementary to capture probe 8, and the arresting linker 73 5-methyl-N$^4$(6-oxyhexyl)-2'-deoxycytidine. Primer 6 consists of a sequence 61 complementary to the other strand of the HBV genome, a portion complementary to labeling probe sequence 10, and the arresting linker 63 5-methyl-N$^4$(6-oxyhexyl)-2'-deoxycytidine.

Sequence 61 was (from the arresting linker) TTG TTC CCA AGA ATA TGG. Sequence 71 was a mixture of two sequences (to the arresting linker): TAC (T/A)GC ACT CAG GCA AGC.

F. Bead Assay Procedure

Ten μL samples of serum or plasma (or standard analyte) are placed in 1.5 mL Eppendorf tubes and treated with 12.5 μL of proteinase K/SDS (as described in *Gene* (1987) 61:254) at 37° C. for 30 min. To each sample, 5 μL of 1M NaOH containing 50 fmoles each of the 5 capture probes are added and the tubes are heated to 100° C. for 10 min. The samples are set on ice for 5 min, microfuged for 10 sec and neutralized with 0.38M acetic acid, 12.3× SSC (final 4× SSC). Annealing of the probes to the analyte is conducted at 55° C. for 1 h. Subsequently, 25 μL of the capture beads are added and the solution is left at 55° C. for an additional 15 min. The beads are washed twice with 500 μL of 0.1% SDS, 4× SSC.

At this point, primers 6 and 7 are added, in addition to PCR reagents (suitable polymerase, nucleotide triphosphates, and the like), and the HBV sequence bracketed by the primers is amplified. PCR is performed using 50 pm of each primer and 400 μM dNTPs, as described by R. Higuchi et al, *Nature* (1988) 332:543, and R. Saiki et al, *Science* (1988) 239:487. Denaturation is conducted at 94° C. for 30 sec, primer annealing at 50° C. for 30 sec, and *Taq* polymerase (commercially available from Perkin-Elmer Cetus) extension at 72° C. for 1.0 min. The bound analyte may optionally be displaced, for example by incubating at 55° C. for 15 minutes in PCR buffer with a displacement probe (5 in FIG. 1) complementary to the common portion of capture probes 2a–c.

The solution is adjusted to 4× SSC, 0.1% SDS, set at 55° C. for 15 min, then washed as above.

Labeling is conducted with 20 μL containing 250 fmoles of labeling probe 10 in HM for 1 h at 37° C. After three washes, the beads are thoroughly drained by inversion onto Kimwipes, treated with the appropriate substrate and measured as described below.

For AP detection, an enzyme-triggered dioxetane (Schaap et al, *Tetrahedron Lett* (1987) 28:1159–1162 and EPA Publication No. 0254051), obtained from Lumigen Inc., is employed. The detection procedure is as follows: For the labeling step 20 μL HM buffer with the AP probe is added to the labeled analyte, and incubated at 55° C. for 15 min. The supernatant is removed and the beads were washed 2× with 380 μL of 0.1× SSC-0.1% SDS. The beads are then washed 2× with 380 μL of 0.1× SSC to remove any remaining SDS. Twenty μL of $3.3 \times 10^{-4}$ M dioxetane in CTAB buffer is added to each aliquot of beads. The beads are tapped lightly so that the reagent falls to the bottom and gently swirled, and incubated in a 37° C. oven for one hour. The beads are then read with a luminometer.

What is claimed:

1. A method for detecting an analyte polynucleotide strand having an analyte sequence within a sample containing polynucleotides, which method comprises:
    a) contacting said analyte polynucleotide with a capture probe under hybridization conditions to form an analyte-capture probe complex, said capture probe comprising an analyte-binding region and a first specific binding partner, said analyte-binding region hybridizable with a region of said analyte polynucleotide, and said first specific binding partner having specificity for a second binding partner;
    b) contacting said first specific binding partner with said second binding partner, wherein said second binding partner is immobilized on a first support, whereby said analyte-capture probe complex is immobilized at said first support to provide an immobilized analyte-capture probe complex;
    c) separating nonbound polynucleotides from said immobilized analyte-capture probe complex;
    d) contacting said analyte polynucleotide with a first primer complementary to a first primer-binding region of said analyte polynucleotide under hybridizing conditions, said first primer comprising an analyte-hybridizing region and a third specific binding partner separated from one another by means for halting transcription therebetween;
    e) initiating nucleotide polymerization with polymerization means at said first primer to form an analyte-complementary strand duplex said complementary strand complementary to said analyte but not to said third specific binding partner;
    f) denaturing said analyte-complementary strand duplex to yield said complementary strand separated from said analyte polynucleotide;
    g) contacting said complementary strand with a second primer capable of hybridizing to a second primer-binding region of said complementary strand, and contacting said analyte polynucleotide with said first primer;
    h) initiating nucleotide polymerization with polymerization means to form an analyte-copy duplex having a strand complementary to a region of said complementary strand containing said first primer-binding region, and an analyte-complementary strand duplex;
    i) repeating steps f-h using the product of step h in place of the analyte-complementary strand duplex of step e to provide an amplified product comprising said first and second primers, amplified amounts of said analyte polynucleotide and a polynucleotide sequence complementary to said analyte sequence; and
    j) detecting said amplified product.

2. The method of claim 1, wherein said first specific binding partner comprises a first polynucleotide strand having a sequence which is not complementary to said analyte, polynucleotide said second binding partner comprises a second polynucleotide strand having a sequence which is complementary to said first binding partner polynucleotide strand and is not complementary to said analyte polynucleotide and wherein the means for halting transcription in said first primer is an arresting linker.

3. The method of claim 2, wherein said analyte polynucleotide is displaced from said first support by hybridizing to said second binding partner polynucleotide strand a displacing polynucleotide strand having a region complementary to said second binding partner polynucleotide strand.

4. The method of claim 2, wherein said analyte polynucleotide is displaced from said first support by hybridizing to said first binding partner polynucleotide strand a displacing polynucleotide strand having a region complementary to said first binding partner polynucleotide strand.

5. The method of claim 1, wherein said first primer further comprises at its 3' end a third binding partner, said third binding partner specifically binding to a fourth binding partner, wherein said fourth binding partner is bound to a solid support and wherein the means for halting transcription in said first primer is an arresting linker.

6. The method of claim 5, wherein said detecting step comprises:
   contacting said amplified product with a solid support having said fourth binding partner bound thereto, and hybridizing said third binding partner to said fourth binding partner, to provide an immobilized amplified product;
   separating non-bound polynucleotides from said immobilized amplified product; and
   detecting the presence of said amplified product.

7. The method of claim 6 wherein said third binding partner comprises a third polynucleotide strand having a sequence which is not complementary to said analyte polynucleotide coupled to said primer by an arresting linker, and said fourth binding partner comprises a fourth polynucleotide strand having a sequence which is complementary to said third binding partner polynucleotide strand and is not complementary to said analyte polynucleotide.

8. The method of claim 6 wherein said second primer further comprises a fifth specific binding partner at its 3' end coupled to said primer by an arresting linker, capable of specifically binding to a sixth binding partner, wherein said sixth binding partner is bound to a detectable label.

9. The method of claim 8, wherein said detecting step further comprises:
   contacting said immobilized amplified product with said labeled sixth binding partner;
   separating non-bound sixth binding partner; and
   determining the presence of bound sixth binding partner.

10. The method of claim 8 wherein said fifth binding partner comprises a fifth polynucleotide strand having a sequence which is not complementary to said analyte strand, and said sixth binding partner comprises a sixth polynucleotide strand having a sequence which is complementary to said fifth binding partner polynucleotide strand and it not complementary to said analyte polynucleotide or said analyte-complementary strand.

11. The method of claim 1, wherein said second primer further comprises at its 3' end a third binding partner coupled to said primer by an arresting linker, wherein said third binding partner is capable of specifically binding a fourth binding partner, wherein said fourth binding partner is bound to a support.

12. The method of claim 11, wherein said detecting step comprises:
   contacting said amplified product with a solid support having said fourth binding partner bound thereto, and hybridizing said third binding partner to said fourth binding partner, to provide an immobilized amplified product;
   separating non-bound polynucleotides from said immobilized amplified product; and
   detecting the presence of said amplified product.

13. The method of claim 11 wherein said third binding partner comprises a third polynucleotide strand having a sequence which is not complementary to said analyte strand, and said fourth binding partner comprises a fourth polynucleotide strand having a sequence which is complementary to said third binding partner polynucleotide strand and is not complementary to said analyte polynucleotide or said analyte-complementary strand.

14. The method of claim 11 wherein said first primer further comprises a fifth specific binding partner at its 3' end, coupled to said primer by an arresting linker, wherein said fifth specific binding partner is capable of specifically binding to a sixth binding partner, wherein said sixth binding partner is bound to a detectable label.

15. The method of claim 14, wherein said detecting step comprises:
   contacting said immobilized amplified product with said labeled sixth binding partner;
   separating non-bound sixth binding partner; and
   determining the presence of bound sixth binding partner.

16. The method of claim 14 wherein said fifth binding partner comprises a fifth polynucleotide strand having a sequence which is not complementary to said analyte strand, and said sixth binding partner comprises a sixth polynucleotide strand having a sequence which is complementary to said fifth binding partner polynucleotide strand and is not complementary to said analyte polynucleotide or said analyte-complementary strand.

17. The method of claim 1, which further comprises amplifying said analyte polynucleotide with third and fourth primers prior to contacting said analyte polynucleotide with said first primer, wherein said third and fourth primers hybridize to regions of said analyte polynucleotide and the complement of said analyte polynucleotide outside the region bounded by said first primer-binding region bounded by said first primer-binding region and second primer-binding region, thus amplifying the portion of the analyte polynucleotide and its complement which contains the analyte sequence and the first and second primer-binding regions.

18. An assay kit for amplifying and detecting an analyte polynucleotide strand having an analyte sequence within a sample containing polynucleotides, which kit comprises a package for:
   a capture probe, said capture probe comprising an analyte-binding sequence complementary to a region of said analyte polynucleotide coupled to a displaceable first specific binding partner;
   a first support, having bound thereto a second binding partner specific for said first partner;
   a first primer complementary to a first primer-binding region of said analyte polynucleotide; and
   a second primer complementary to a second primer-binding region of said analyte-complementary strand, wherein said second primer-binding region does not substantially overlap said first primer-binding region and wherein said first binding partner comprises a first polynucleotide strand having a sequence which is not complementary to said analyte strand coupled to said primer by an arresting linker, and said second binding partner comprises a second polynucleotide strand having a sequence which is complementary to said first binding partner polynucleotide strand and is not complementary to said analyte strand.

19. The assay kit of claim 18, which further comprises a displacing polynucleotide having a region complementary to said second binding partner polynucleotide.

20. The assay kit of claim 18, wherein said first primer further comprises at its 3' end a third binding partner capable of specifically binding a fourth binding partner coupled to said primer by an arresting linker, and
   wherein said kit further comprises a support having said fourth binding partner bound thereto.

21. The assay kit of claim 20, wherein said second primer further comprises a fifth specific binding partner at its 3' end coupled to said primer by an arresting linker, capable of specifically binding to a sixth binding partner, and wherein said kit further comprises a sixth binding partner bound to a detectable label.

22. The assay kit of claim 18, wherein said second primer further comprises at its 3' end a third binding partner coupled to said primer by an arresting linker, wherein said third binding partner is capable of specifically binding a fourth binding partner, and wherein said kit further comprises a second support having said fourth binding partner bound thereto.

23. The assay kit of claim 22, wherein said first primer further comprises a fifth specific binding partner coupled to said primer by an arresting linker, wherein said fifth specific binding partner is capable of specifically binding a sixth binding partner, and wherein said kit further comprises a sixth binding partner bound to a detectable label.

24. The assay kit of claim 18, which further comprises third and fourth primers complementary to said analyte polynucleotide and the complement thereof, wherein said third and fourth primers hybridize to regions of the analyte polynucleotide and its complement which are outside the region bounded by said first primer-binding region and second primer-binding region.

* * * * *